US011350847B2

(12) United States Patent
Bar-Tal et al.

(10) Patent No.: US 11,350,847 B2
(45) Date of Patent: Jun. 7, 2022

(54) COMPOSITE VISUALIZATION OF BODY PART

(71) Applicant: Biosense Webster (Israel) Ltd., Yokneam (IL)

(72) Inventors: Meir Bar-Tal, Haifa (IL); Aharon Turgeman, Zichron Ya'acov (IL); Benjamin Cohen, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 344 days.

(21) Appl. No.: 16/219,427

(22) Filed: Dec. 13, 2018

(65) Prior Publication Data

US 2020/0187825 A1 Jun. 18, 2020

(51) Int. Cl.
| | |
|---|---|
| *A61B 5/06* | (2006.01) |
| *A61B 34/10* | (2016.01) |
| *A61B 90/00* | (2016.01) |
| *A61B 5/053* | (2021.01) |
| *A61B 18/14* | (2006.01) |

(Continued)

(52) U.S. Cl.
CPC .............. *A61B 5/065* (2013.01); *A61B 5/053* (2013.01); *A61B 18/1492* (2013.01); *A61B 34/10* (2016.02); *A61B 90/37* (2016.02); *A61B 5/6852* (2013.01); *A61B 2018/00351* (2013.01);

(Continued)

(58) Field of Classification Search
CPC ......... A61B 5/015; A61B 5/053; A61B 5/065; A61B 5/6852; A61B 34/10; A61B 34/20; A61B 90/37; A61B 18/1492
See application file for complete search history.

(56) References Cited

U.S. PATENT DOCUMENTS

| | | | |
|---|---|---|---|
| 7,536,218 B2 | 5/2009 | Govari et al. | |
| 7,756,576 B2 | 7/2010 | Levin | |

(Continued)

FOREIGN PATENT DOCUMENTS

EP        3026639 A1      6/2016

OTHER PUBLICATIONS

"Multi-Part Modeling and Segmentation of Left Atrium in C-Arm CT for Image-Guided Ablation of Atrial Fibrillation" by Y. Zheng et al. IEEE Trans Med Imag. vol. 33, No. 2. pp. 318-331, Feb. 2014 (Year: 2014).*

(Continued)

*Primary Examiner* — Jason M Ip
(74) *Attorney, Agent, or Firm* — Dergosits & Noah LLP; Todd A. Noah (57) ABSTRACT

In one embodiment, a body part visualization system includes a medical instrument configured to be inserted into a body part of a living subject, a display, and processing circuitry configured to compute location coordinates of the medical instrument in the body part, and render to the display a first three-dimensional (3D) representation of the body part, the first 3D representation showing an external surface of the body part with a moving window, which moves over the external surface in the first 3D representation responsively to the computed location coordinates of the medical instrument so as to provide, via the window, an internal view of the first 3D representation of the body part, the internal view including a second 3D representation of at least a part of the medical instrument at the computed location coordinates.

19 Claims, 7 Drawing Sheets

(51) Int. Cl.
*A61B 5/00* (2006.01)
*A61B 18/00* (2006.01)

(52) U.S. Cl.
CPC .............. *A61B 2018/00577* (2013.01); *A61B 2090/3782* (2016.02); *G06T 2210/41* (2013.01)

(56) References Cited

U.S. PATENT DOCUMENTS

| | | |
|---|---|---|
| 2009/0143677 A1 | 6/2009 | Govari et al. |
| 2010/0149213 A1 | 6/2010 | Navab |
| 2010/0312096 A1* | 12/2010 | Guttman ................ A61B 34/10 600/411 |
| 2013/0184569 A1* | 7/2013 | Strommer .............. A61B 5/042 600/424 |
| 2013/0245461 A1 | 9/2013 | Maier-Hein et al. |
| 2014/0180101 A1 | 6/2014 | Hadjicostis |
| 2017/0035287 A1 | 2/2017 | Ren |
| 2017/0140527 A1 | 5/2017 | Govari |
| 2017/0258526 A1 | 9/2017 | Lang |
| 2018/0182157 A1 | 6/2018 | Zar et al. |

OTHER PUBLICATIONS

"The Trans-Visible Navigator: A See-Through Neuronavigation System Using Augmented Reality" by E. Watanabe. World Neurosurgery. vol. 87, pp. 399-405, Mar. 2016 (Year: 2016).*
European Search report for corresponding EPA No. 19215467.2 dated Apr. 17, 2020.

\* cited by examiner

COMPOSITE VISUALIZATION OF BODY PART

FIELD OF THE INVENTION

The present invention relates to visualization of body parts, and in particular, but not exclusively to, visualization of body parts with medical instruments.

BACKGROUND

Body parts are mapped to provide information to a physician. By way of example, cardiac mapping is performed to visualize various features of different parts of the heart, including indicating surfaces of tissue, electrical features such as local activation times (LATs) using color maps and/or arrows, and medical treatment features using tags, such as VisiTags of Biosense Webster®, Inc. of Irvine, Calif., United States. A VisiTag indicates a location of an ablation performed by a catheter. The VisiTag may also include additional information such as ablation time used to create the ablation. VisiTag location information may be useful for making future ablation decisions, by way of example only. Medical instruments may also be visualized along with the cardiac map.

US Patent Publication 2017/0258526 of Lang describes devices and methods for performing a surgical step or surgical procedure with visual guidance using an optical head mounted display.

US Patent Publication 2009/0143677 of Govari, et al., describes a method for imaging an anatomical structure on a display, including acquiring an initial spatial representation of the anatomical structure and positioning an instrument in proximity to the anatomical structure. The method further includes determining a location of the instrument, and generating, in response to the location, an image of a part of the anatomical structure. The method includes appending the image to the initial spatial representation to display a combined spatial representation.

US Patent Publication 2014/0180101 of Hadjicostis describes a method of ablating plaque from an artery section, using a catheter having a longitudinal body and a distal imaging and ablation tip connected to a distal end of the longitudinal body. The tip has an ultrasound imaging array, and a distal, forward directed face, distal to the ultrasound imaging array, and including a set of electrodes arranged circumferentially about the distal face. The catheter further includes a set of conductors connected to the tip and extending through the body. The catheter is connected to an image display. In the method the tip is introduced into the artery section and images the artery section in front, thereby creating imagery of the artery, which is shown on the image display. This imagery is reviewed and in reliance thereon selectively the electrodes are selectively activated to ablate plaque, while not activating any electrode that would damage any bare arterial wall.

US Patent Publication 2013/0245461 of Maier-Hein, et al., describes a sensor means employed to sense a distance to the surface of a subject to be examined, so that a range image may be acquired. Intensity information may be acquired alongside the distance information. The distance information and intensity information may be evaluated to track the pose of the sensor means relative to the surface of the subject to be examined, so that anatomical data related to said subject may be displayed as seen from the position and/or orientation of the sensor means or display means. By moving the sensor means or display means along the surface of the subject to be examined, such as a patient in a hospital environment, the user hence gets the impression of being able to look directly into the human body.

SUMMARY

There is provided in accordance with an embodiment of the present disclosure a body part visualization system, including a medical instrument configured to be inserted into a body part of a living subject, a display, and processing circuitry configured to compute location coordinates of the medical instrument in the body part, and render to the display a first three-dimensional (3D) representation of the body part, the first 3D representation showing an external surface of the body part with a moving window, which moves over the external surface in the first 3D representation responsively to the computed location coordinates of the medical instrument so as to provide, via the window, an internal view of the first 3D representation of the body part, the internal view including a second 3D representation of at least a part of the medical instrument at the computed location coordinates.

Further in accordance with an embodiment of the present disclosure the moving window includes a mesh which follows the contours of a part of the external surface replaced by the moving window.

Still further in accordance with an embodiment of the present disclosure the mesh is at least partially colored to correspond to colored patches allocated to the part of the external surface.

Additionally, in accordance with an embodiment of the present disclosure the internal view includes colored patches disposed on an internal surface of the first 3D representation.

Moreover, in accordance with an embodiment of the present disclosure the processing circuitry is configured to project a point of the medical instrument onto the external surface of the first 3D representation, and define a perimeter of the moving window centered around the projected point.

Further in accordance with an embodiment of the present disclosure the processing circuitry is configured to project the point of the medical instrument onto the external surface in a direction substantially perpendicular to the external surface.

Still further in accordance with an embodiment of the present disclosure the processing circuitry is configured to define locations on the perimeter as terminating at the ends of respective equidistant geodesic lines from the projected point.

Additionally, in accordance with an embodiment of the present disclosure the internal view includes at least one element in addition to the second 3D representation of at least the part of the medical instrument.

Moreover, in accordance with an embodiment of the present disclosure the body part is a chamber of a heart, the medical instrument including an ablation probe having an electrode configured to apply radio-frequency radiation to a myocardium of the chamber so as to ablate the myocardium.

Further in accordance with an embodiment of the present disclosure the at least one element includes a graphical symbol marking a location of an ablation performed by the ablation probe.

There is also provided in accordance with still another embodiment of the present disclosure a body part visualization method, including computing location coordinates of a medical instrument in a body part of a living subject, and rendering to a display a first three-dimensional (3D) representation of the body part, the first 3D representation showing an external surface of the body part with a moving window, which moves over the external surface in the first 3D representation responsively to the computed location coordinates of the medical instrument so as to provide, via the window, an internal view of the first 3D representation of the body part, the internal view including a second 3D representation of at least a part of the medical instrument at the computed location coordinates.

Still further in accordance with an embodiment of the present disclosure the moving window includes a mesh which follows the contours of a part of the external surface replaced by the moving window.

Additionally, in accordance with an embodiment of the present disclosure the mesh is at least partially colored to correspond to colored patches allocated to the part of the external surface.

Moreover, in accordance with an embodiment of the present disclosure the internal view includes colored patches disposed on an internal surface of the first 3D representation.

Further in accordance with an embodiment of the present disclosure, the method includes projecting a point of the medical instrument onto the external surface of the first 3D representation, and defining a perimeter of the moving window centered around the projected point.

Still further in accordance with an embodiment of the present disclosure the projecting including projecting the point of the medical instrument onto the external surface in a direction substantially perpendicular to the external surface.

Additionally, in accordance with an embodiment of the present disclosure, the method includes defining locations on the perimeter as terminating at the ends of respective equidistant geodesic lines from the projected point.

Moreover, in accordance with an embodiment of the present disclosure the internal view includes at least one element in addition to the second 3D representation of at least the part of the medical instrument.

Further in accordance with an embodiment of the present disclosure the body part is a chamber of a heart, the medical instrument including an ablation probe having an electrode configured to apply radio-frequency radiation to a myocardium of the chamber so as to ablate the myocardium.

Still further in accordance with an embodiment of the present disclosure the at least one element includes a graphical symbol marking a location of an ablation performed by the ablation probe.

There is also provided in accordance with still another embodiment of the present disclosure a software product, including a non-transient computer-readable medium in which program instructions are stored, which instructions, when read by a central processing unit (CPU), cause the CPU to compute location coordinates of a medical instrument in a body part of a living subject, and render to a display a first three-dimensional (3D) representation of the body part, the first 3D representation showing an external surface of the body part with a moving window, which moves over the external surface in the first 3D representation responsively to the computed location coordinates of the medical instrument so as to provide, via the window, an internal view of the first 3D representation of the body part, the internal view including a second 3D representation of at least a part of the medical instrument at the computed location coordinates.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Body-part mapping may provide an external view of a body part, e.g., looking at the outside of the heart. Additional information such as color maps and/or VisiTags may also be disposed in the external view of the body part. Body part mapping may alternatively provide an internal view of the body part, e.g., providing an internal view of a chamber of the heart or an artery. Additional information such as color maps and VisiTags may also be disposed in the internal view of the body part. As useful as the external views and internal views are to a physician, the separate views do not provide the physician with the context of the external view while viewing the internal view, and vice-versa.

Additionally, some information may be partially included in the external view and partially included in the internal view. For example, Carto® ablation systems of Biosense Webster, Inc. of Irvine, Calif., United States, may generate a VisiTag which provides the position, and other information, regarding the ablation. A VisiTag is generally incorporated into the map of the heart chamber where the ablation has been performed. VisiTags may be used for a variety of diagnostic purposes, for example, but not limited to, determining positions where ablation along a planned ablation line has not been performed in order to ablate the non-ablated positions and/or not to re-ablate already ablated positions.

A VisiTag may be disposed on the map according to an average position of the ablation. Thus, in some instances a VisiTag may be disposed in an external view of the heart chamber and in other instances a VisiTag may be disposed in the internal view of the heart chamber. Therefore, in many cases, neither the external view nor the internal view shows all the VisiTags generated by the system.

Embodiments of the present invention provide a partial external view and a partial internal view of a three-dimensional 3D body part map or representation allowing a physician to view the 3D map of the body part while simultaneously keeping the context of the external view and the internal view together. In addition to seeing the shape of the body part (e.g., via contours) other external and internal elements such as medical instruments, tags (e.g., VisiTags) and/or mapping colors may also be visualized together.

The combined external and internal view is implemented using a moving window which moves over an external surface of the 3D map according to tracked movement of a medical instrument inside the body part, so as the medical instrument is moved in the body part, the window is moved in a corresponding fashion. The internal view is provided through the moving window and shows internal elements such as internal anatomical features of the body part, a representation of the medical instrument, colored patches, and tags, e.g., VisiTags. In this manner, the relevant portion of the internal view is displayed with the external view. By way of example only, the medical instrument may include any one or more of the following, a probe for inserting into the body-part, an endoscope, and/or a surgical tool such as an ear, nose and throat (ENT) tool, suction tool, microdebrider, or shaver.

The moving window may optionally include a mesh having a mesh fabric which follows the contours of a part of the external surface replaced by the moving window. The mesh fabric may be at least partially colored to correspond to colored patches allocated to the part of the external surface replaced by the moving window.

The moving window may be generated based on projecting a point (e.g., such as a tip) of the medical instrument onto a part of the external surface of the 3D map currently being displayed (e.g., in a direction substantially perpendicular (e.g., within 5 degrees accuracy) to the external surface) and then define locations of a perimeter of the moving window according to ends of respective equidistant (e.g., geodesic or straight) lines from the projected point. In the above example, the moving window has a generally circular shape. In some embodiments, the moving window may have any suitable shape.

The examples described hereinbelow generally relate to cardiac mapping. Embodiments of the present invention may be implemented for mapping any suitable body part, e.g., for sinus procedures, providing a combined external and internal view using the moving window to provide a view of the map of the body part while simultaneously keeping the context of the external view and the internal view together.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 1:
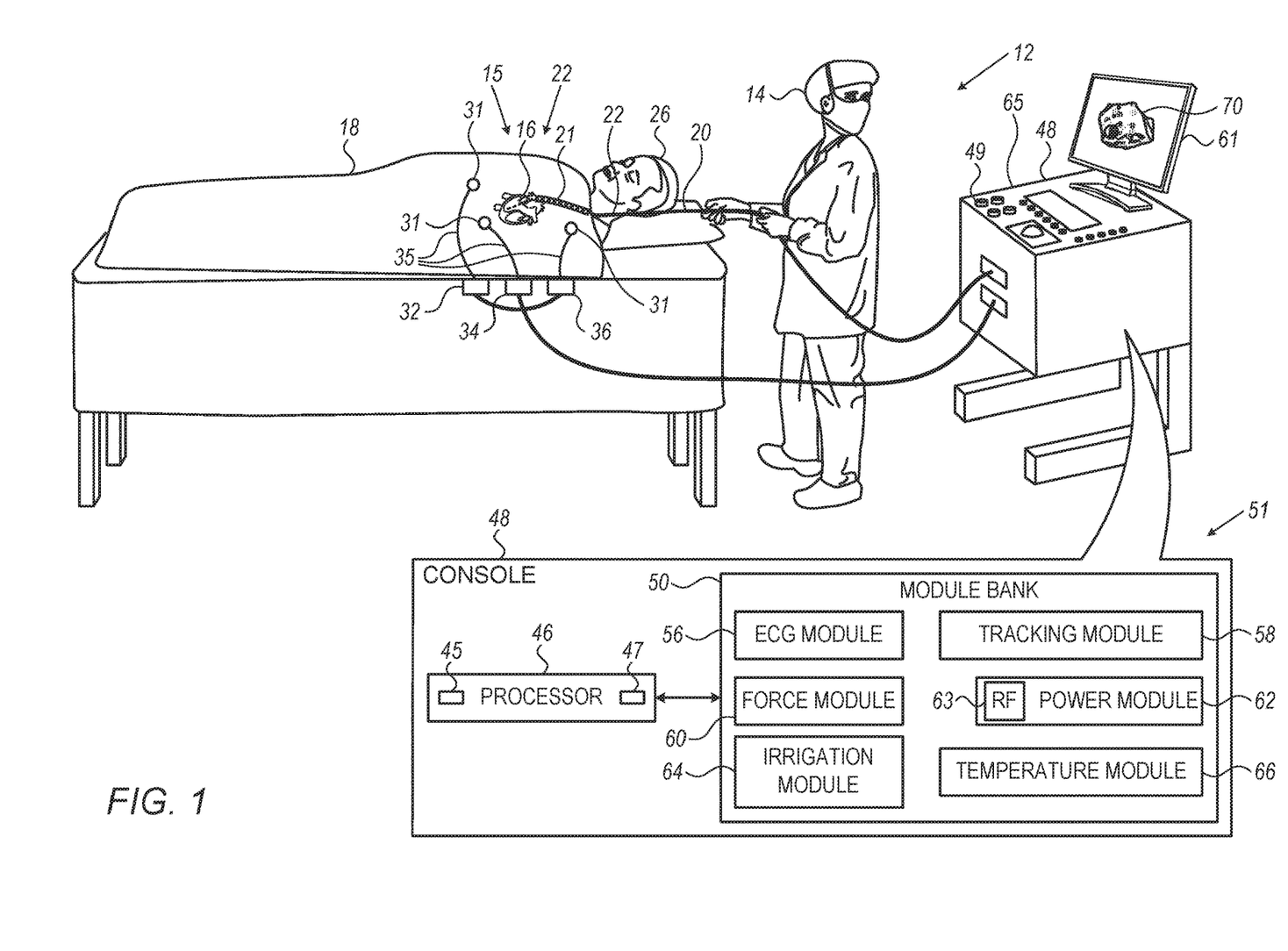
FIG. 1 a schematic illustration of an invasive medical procedure using an apparatus according to an embodiment of the present invention.
Figure 2:
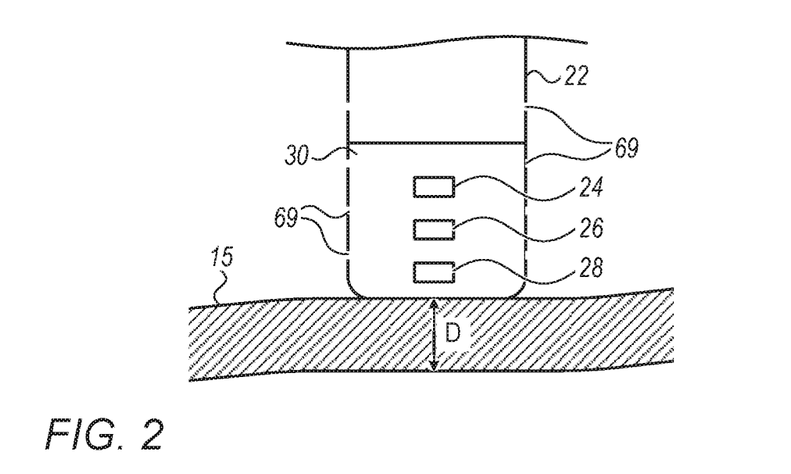
FIG. 2 is a schematic illustration of a distal end of a probe used in the apparatus of FIG. 1 according to an embodiment of the present invention.

Reference is now made to FIG. 1, which is a schematic illustration of an invasive medical procedure using an apparatus 12 including a body part visualization subsystem according to an embodiment of the present invention. Reference is also made to FIG. 2, which is a schematic illustration of a distal end 22 of a probe 20 used in the apparatus 12 according to an embodiment of the present invention. The procedure is performed by a physician 14, and in the description hereinbelow the procedure is assumed to comprise an ablation of a portion of tissue 15 of a myocardium 16 of the heart of a human patient 18.

In order to perform the investigation, the physician 14 inserts the probe 20 into a sheath 21 that has been pre-positioned in a lumen of the patient 18 so that the probe 20 is inserted into a chamber of the heart. The sheath 21 is positioned so that the distal end 22 of the probe 20 enters the heart of the patient 18. The distal end 22 comprises a position sensor 24 that enables the location and orientation of the distal end 22 to be tracked, a force sensor 26 that measures the force applied by the distal end 22 when it contacts the myocardium 16, and one or more temperature sensors 28 that measure the temperature at respective locations of the distal end 22. The distal end 22 also comprises one or more electrodes 30 which are used to apply radiofrequency power to the myocardium 16 in the chamber so as to ablate the myocardium 16. The electrode(s) 30 may also be used to acquire electropotentials from the myocardium 16.

The apparatus 12 is controlled by a system processor 46, which is located in an operating console 48 of the apparatus. The operating console 48 comprises controls of at least one user input device 49 which are used by the physician 14 to communicate with the processor 46. The software for processor 46 may be downloaded to the processor 46 in electronic form, over a network, for example. Alternatively, or additionally, the software may be provided on non-transitory tangible media, such as optical, magnetic, or electronic storage media.

The processor 46 may comprise real-time noise reduction circuitry 45, typically configured as a field programmable gate array (FPGA), followed by an analog-to-digital (A/D) signal conversion integrated circuit 47. The processor 46 can pass the signal from the A/D signal conversion integrated circuit 47 to another processor and/or can be programmed to perform at least one algorithm disclosed herein, the algorithm comprising steps described hereinbelow. The processor 46 uses the noise reduction circuitry 45 and the A/D signal conversion integrated circuit 47, as well as features of modules which are described in more detail below, in order to perform the algorithm.

In order to operate the apparatus 12, the algorithm of the processor 46 communicates with a module bank 50, which has a number of modules used by the processor 46 to operate the apparatus 12. Thus, the module bank 50 comprises an electrocardiograph (ECG) module 56 coupled to receive signals from body surface electrodes 31 and/or electrodes 30, in order to provide the ECG signals to the processor 46. The body surface electrodes 31 and/or the electrode(s) 30 are configured for application to a body of a subject (e.g., the patient 18) and configured to output signals in response to electrical activity of a heart of the subject. The electrode(s) 30 is applied to the heart of the body via the probe 20. The module bank 50 also includes a tracking module 58 which receives and analyzes signals from the position sensor 24, and which uses the signal analysis to generate a location and an orientation of the distal end 22. In some embodiments the position sensor 24 comprises one or more coils which provide the sensor signals in response to magnetic fields traversing the coils. In these embodiments, in addition to receiving and analyzing signals from sensor 24, tracking module 58 also controls radiators 32, 34, and 36 which radiate the magnetic fields traversing the position sensor 24. The radiators 32, 34, 36 are positioned in proximity to the myocardium 16, and are configured to radiate alternating magnetic fields into a region in proximity to the myocardium 16. A plurality of wire connections 35 link the operating console 48 with body the surface electrodes 31 and other components (such as the radiators 32, 34, 36 and the sensor 24) to enable the tracking module 58 to measure location and orientation coordinates of the probe 20. In some embodiments, the tracking module 58 is configured to compute a relative location and a relative orientation of the probe 20 with respect to the heart. Magnetic location and orientation tracking is described in U.S. Pat. Nos. 7,756,576 and 7,536,218, which are hereby incorporated by reference. The Carto system produced by Biosense Webster, of 33 Technology Drive, Irvine, Calif. 92618 USA, uses such a magnetic tracking system. The tracking module 58 is not limited to using magnetic based location and orientation tracking. Any suitable location and orientation tracking can be used, such as impedance-based or image-based tracking.

The apparatus 12 may receive image data from an external imaging modality, such as an MRI unit, CT unit or the like and includes image processors that can be incorporated in or invoked by the processor 46 for generating and displaying images. The image data may be registered with the tracking module 58 and a user interface screen 70 combining the received data and positions of the probe 20 may be displayed to the physician 14 on a display 61. For example, the track of the distal end 22 of the probe 20 may be shown on a three-dimensional (3D) representation of the heart of patient 18 that is displayed on the display 61. In some embodiments, the 3D representation of the heart may be at least partially computed based on mapping performed by the probe 20.

The electrode(s) 30 and the body surface electrodes 31 may be used to measure tissue impedance at the ablation site as taught in U.S. Pat. No. 7,536,218, issued to Govari et al., which is herein incorporated by reference.

The module bank 50 also comprises a force module 60, a power module 62, an irrigation module 64, and a temperature module 66. The functions of these modules are explained below. The modules in the module bank 50, and the processor 46, are herein termed processing circuitry 51.

The force module 60 receives signals from the force sensor 26, and from the signals generates a magnitude of the contact force, herein assumed to be measured in grams, exerted by the distal end 22 on the tissue 15. In some embodiments the force sensor 26 is configured so that the signals it provides to the force module 60 enable the force module 60 to evaluate a direction of the force exerted by the distal end 22 on the tissue 15.

The power module 62 comprises a radiofrequency (RF) signal generator 63 which generates the radiofrequency power to be applied by the electrode(s) 30 to ablate the tissue 15 of the myocardium 16. The processor 46 and the power module 62 are able to adjust a power level, herein assumed to be measured in Watts, delivered by the electrode(s) 30, as well as a length of time, measured in seconds, during which the power is delivered.

The irrigation module 64 controls a rate of flow, herein assumed to be measured in mL/min, of irrigation fluid, typically normal saline solution, supplied to the distal end 22 by a pump 65 disposed in the operating console 48. The probe 20 includes an irrigation channel through which to irrigate the myocardium 16. The irrigation fluid is expelled from irrigation holes 69 in the distal end 22. The pump 65 is configured to selectively pump the irrigation fluid into the irrigation channel at an idle rate and at one or more one non-idle rates (higher than the idle rate) according to a status of the ablation procedure.

The temperature module 66 receives a temperature signal provided by the temperature sensor 28 (or by each temperature sensor 28). The temperature signal is indicative of a temperature of the myocardium at a plurality of different times. The temperature module 66 determines the temperatures registered by each of the sensors 28. Typically, in the case of multiple sensors 28 the temperature module 66 determines a mean temperature of the distal end 22. Additionally, in the case of multiple sensors, the temperature module 66 may produce a map of the temperature distribution of the distal end 22.

Reference is now made to FIGS. 3-6, which are different views of the exemplary user interface screen 70 rendered by the apparatus 12 of FIG. 1. The user interface screen 70 is described with reference to a medical instrument which is configured to be inserted into a body part of a living subject. The probe 20 is an example of the medical instrument. However, the medical instrument may include any suitable medical instrument such as, a non-ablation probe for inserting into the body-part, an endoscope, and/or a surgical tool such as an ENT tool, suction tool, microdebrider, or shaver.

The body part may be any suitable body part, for example, but not limited to, a chamber of a heart or a sinus cavity. The user interface screen 70 may be rendered using any suitable processing and display system and is not limited to being rendered by apparatus 12.

Figure 3:
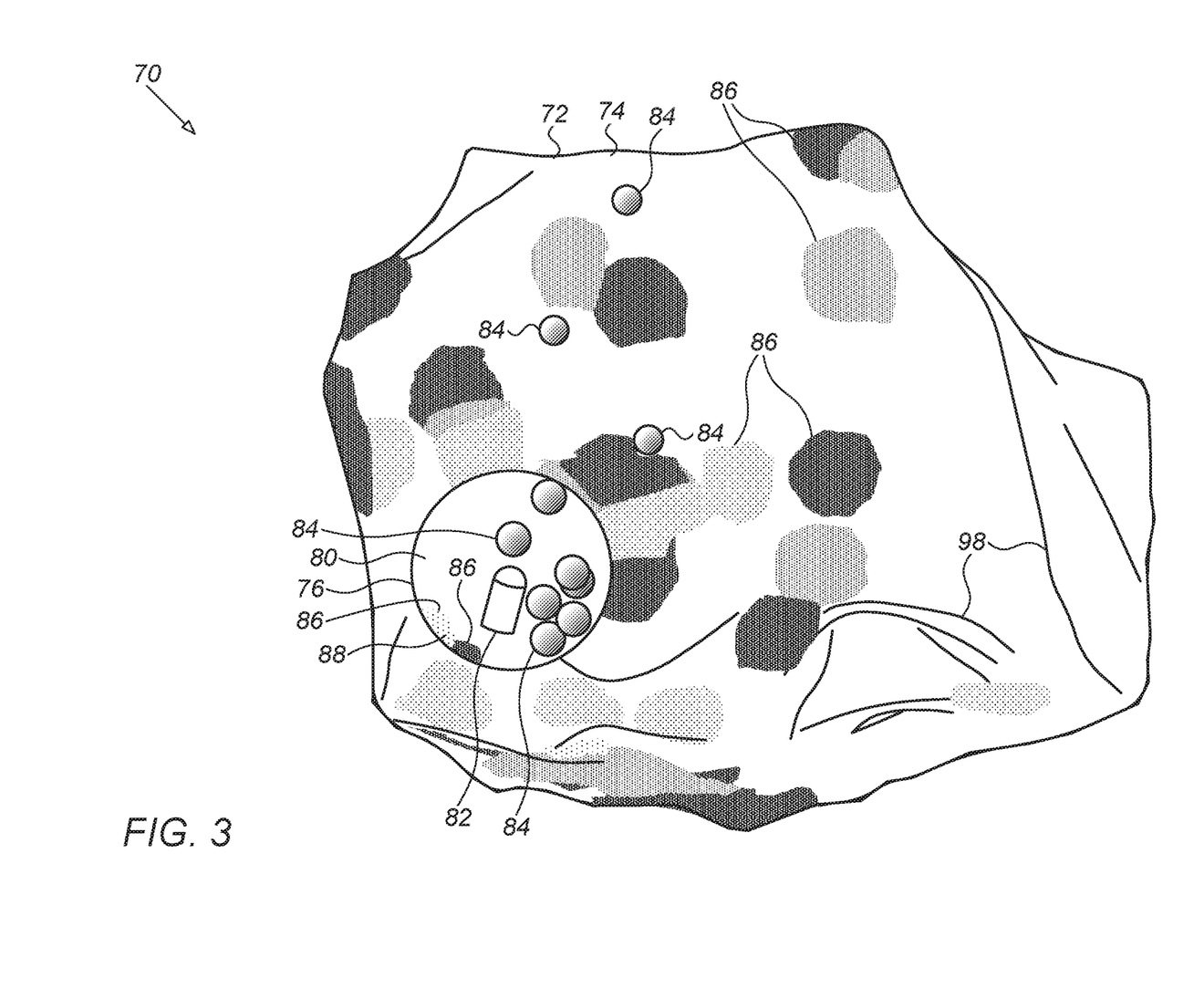
FIGS. 3-6 are different views of an exemplary user interface screen rendered by the apparatus of FIG. 1.

FIG. 3 shows the user interface screen 70 including a 3D representation 72 of the body part. The 3D representation 72 shows an external surface 74 of the body part with contours 98 and a moving window 76, which moves over the external surface 74 in the 3D representation 72 responsively to computed location coordinates of the medical instrument so as to provide, via the window 76, an internal view 80 of the 3D representation 72 of the body part. The moving window 76 therefore moves over the external surface 74 as the medical instrument moves inside the body part. For the sake of simplicity only some of the contours 98 are labeled in the drawings.

The 3D representation 72 of the body part may be rotated and/or zoomed and/or translated by the physician to show any view of the 3D representation 72.

The internal view 80 includes a 3D representation 82 of the medical instrument (or a part thereof) at the computed location coordinates. The internal view 80 may include one or more (2D or 3D) elements in addition to the 3D representation 82 of the medical instrument. The element may include a graphical symbol such as a tag 84, e.g., a VisiTag, which marks a location of an ablation performed by the ablation probe. The external surface 74 may also include one or more addition elements such as the tags 84, e.g., VisiTags. For the sake of simplicity only some of the tags 84 are labeled in the drawings.

The 3D representation 82 and/or the tags 84 may be rendered based on any suitable method for example, but not limited to, using an imaging method described in US Patent Publication 2018/0182157 of Zar, et al which is herein incorporated by reference. In particular, paragraphs 31 to 48 of the Zar, et al. reference describe rendering quadrics over electroanatomical maps. Examples of quadric surfaces include spheres, ellipsoids, cylinders, cones, hyperbolic paraboloids, paraboloids, and hyperboloids. The imaging may include using mechanical data of the medical instrument and combine various quadrics to form an image of the 3D representation 82 of the medical instrument.

The internal view 80 may include colored patches 86 disposed on an internal surface 88 of the 3D representation 72 of the body part. The external surface 74 may also include the colored patches 86 disposed thereon. The colored patches 86 may represent any suitable mapping, e.g., LATs or voltages. The colored patches 86 disposed on the internal surface 88 may represent the same mapping as, or a different mapping from, the colored patches 86 disposed on the external surface 74. For the sake of simplicity only some of the colored patches 86 are labeled in the drawings.

Figure 4:
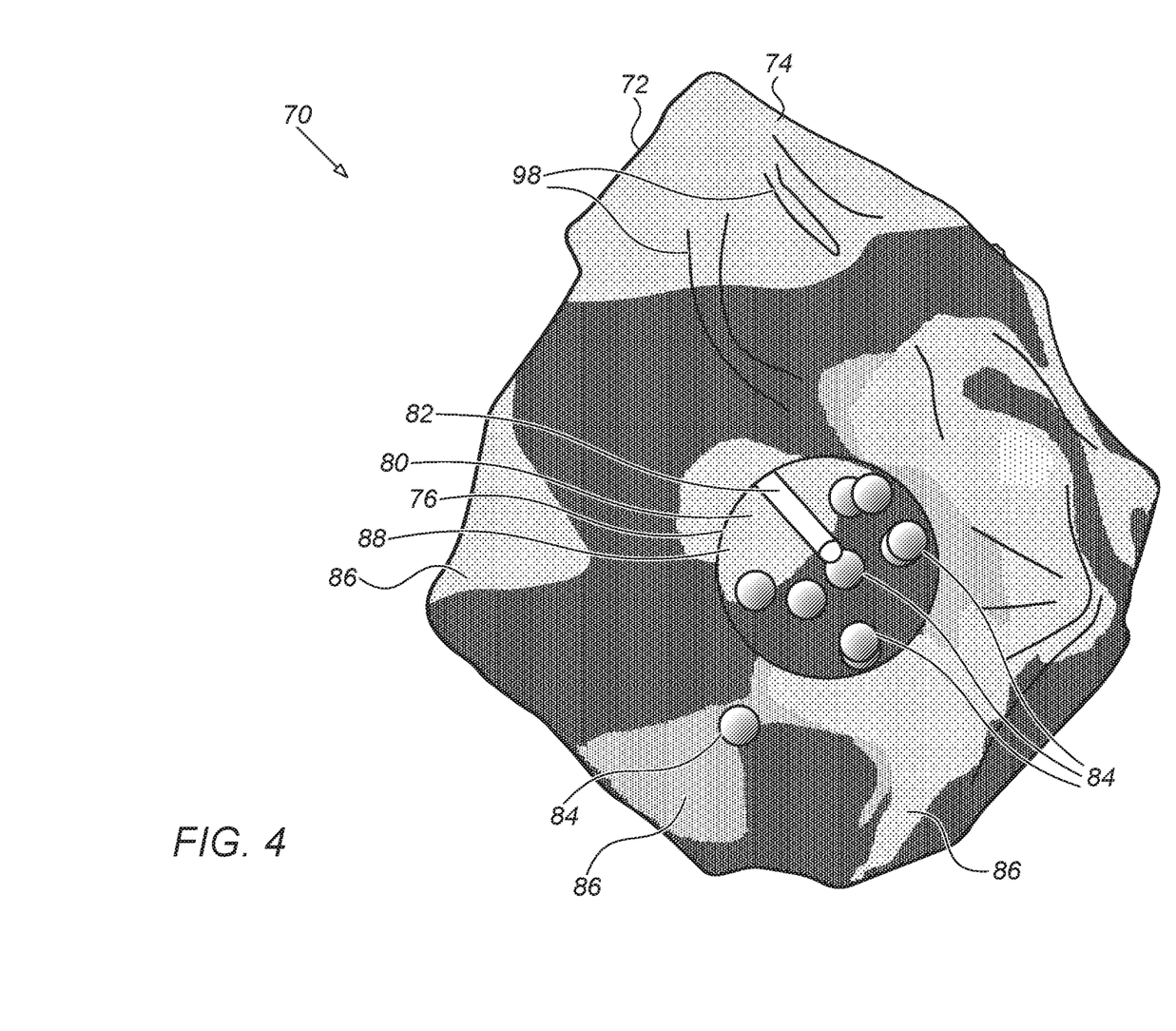

The user interface screen 70 shown in FIG. 4 includes colored patches 86 covering all of the external surface 74 and the internal surface 88.

Figure 5:
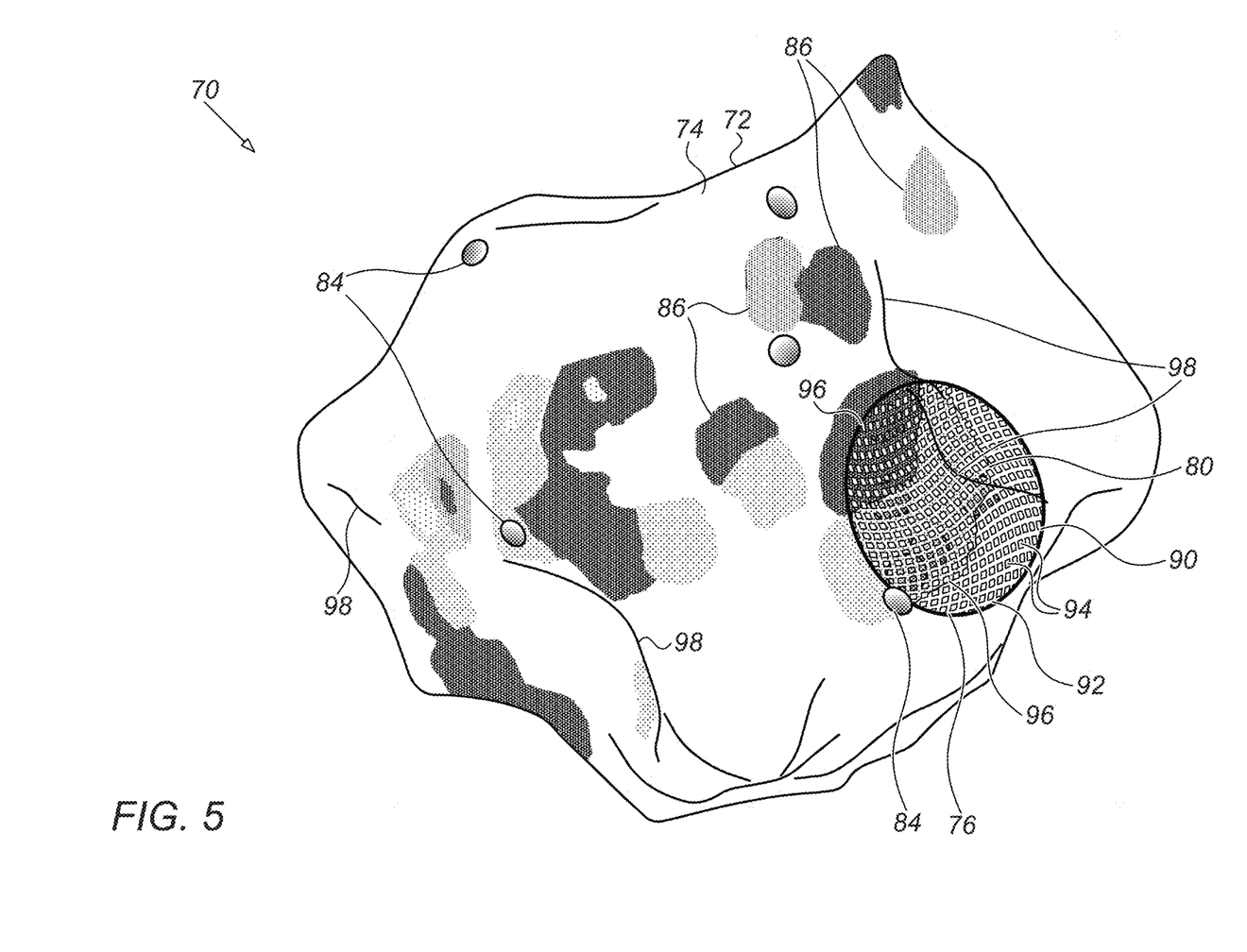
Figure 6:
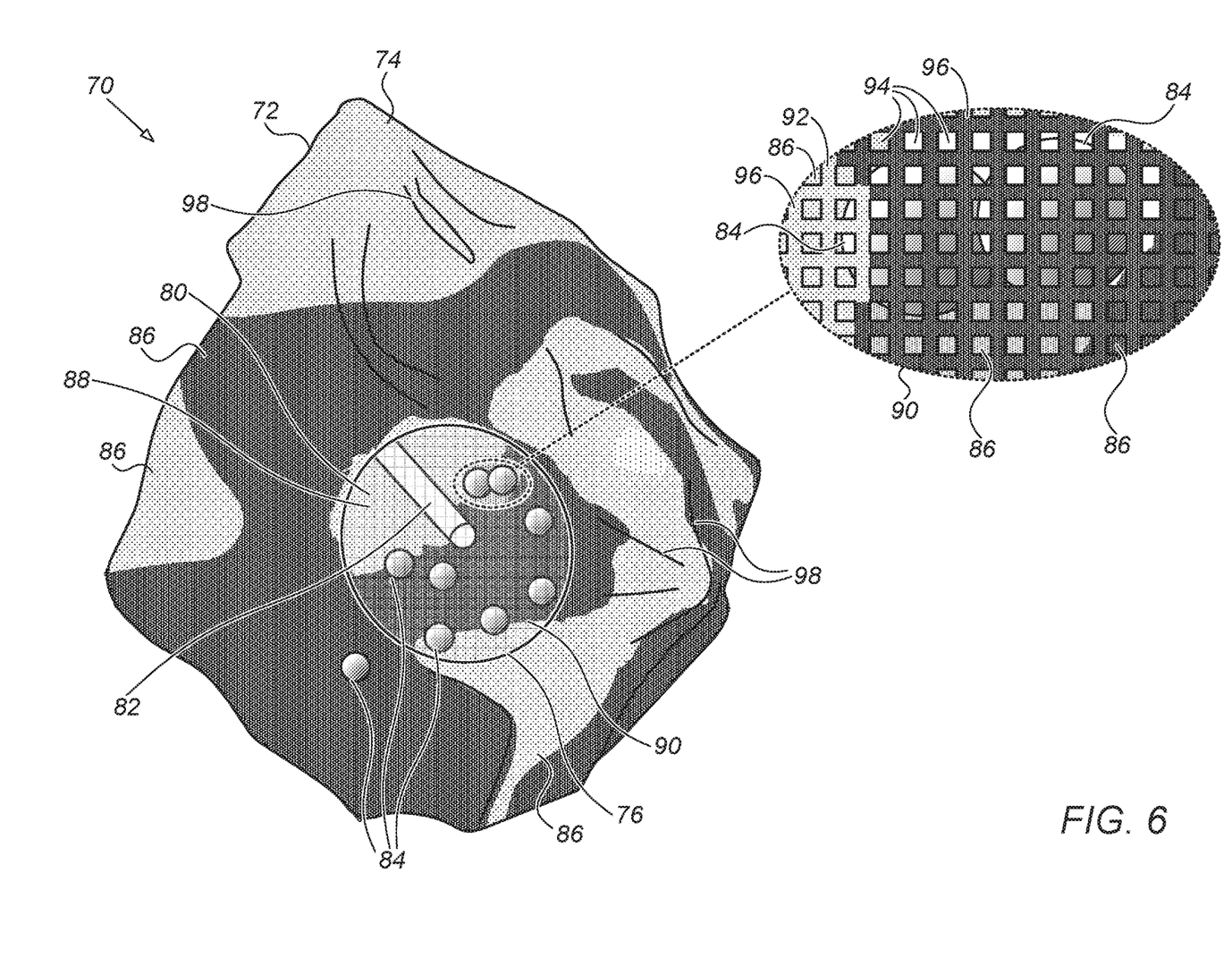

FIGS. 5 and 6 show the moving window 76 including a mesh 90 having a mesh fabric 92, which follows the contours 98 of the part of the external surface 74 replaced by the moving window 76. The mesh 90 includes gaps 94 in the mesh fabric 92. The mesh fabric 92 and its contours aid the physician to retain the context between an external view and the internal view 80 of the body part. The internal view 80 is visible through the gaps 94 in the mesh fabric 92 allowing view of the 3D representation 82 of the medical instrument and the tags 84 through the gaps 94. For the sake of simplicity only some of the gaps 94 are labeled in the drawings.

In FIG. 5, the mesh fabric 92 is partially colored with colored patches 96 corresponding to the colored patches 86 allocated to the part of the external surface 74 replaced by the moving window 76.

In FIG. 6, the mesh fabric 92 is colored with colored patches 96 corresponding to the colored patches 86 allocated to the part of the external surface 74 replaced by the moving window 76. For the sake of simplicity only some of the colored patches 96 are labeled in the drawings. Additionally, some of the gaps 94 in the mesh fabric 92 are colored according to the colored patches 86 disposed on the internal surface 88 of the 3D representation 72 of the body part as seen through the gaps 94.

The moving window 76 may have any suitable shape (e.g., circle, ellipse, or any polygon) and any suitable size. The position of the moving window 76 is computed to include the 3D representation 82 of the medical instrument (or a part thereof such as a distal end of the medical instrument).

In some embodiments the position of the moving window 76 may be computed as follows. A point on the medical instrument (such as a tip or another point on the distal end of the medical instrument) is projected onto the external surface 74 of the 3D representation 72 of the body part. The point is generally projected onto the external surface 74 (currently in view) at a first location, which is closest to the point. Therefore, even if the point is closer to a second location on a part of the external surface 74 not currently in view, the point is still projected on to the external surface 74 (currently in view) at the first location. In other embodiments, if the point is closer to the second location on a part of the external surface 74 not currently in view, the 3D representation 72 of the body part may be rotated by the apparatus 12 so that the second location of the external surface 74 that is closest to the point, and the resulting moving window 76 disposed around the second location, are viewable in the user interface screen 70. In other embodiments, the point is projected on to the external surface 74 in a direction which is substantially perpendicular (e.g., within 5 degrees accuracy) to the external surface 74. A perimeter of the moving window 76 is then centered around the projected point on the external surface 74. In some embodiments, locations on the perimeter of the moving window are defined according to ends of respective equidistant (e.g., geodesic or straight) lines from the projected point so that the moving window 76 has a generally circular shape, which is distorted by the contours of the external surface 74 of the 3D representation 72 of the body part.

Various features of the user interface screen 70 may be user configurable for example, but not limited to, whether the mesh 90 is shown, a design and/or thickness of the mesh fabric 92, a size and/or shape of the gaps 94 in the mesh fabric 92, whether colored patches 86 are shown on the external surface 74 and the mesh fabric 92, whether colored patches 86 are shown on the internal surface 88, a shape of the moving window 76, a size or radius of the moving window 76, whether the distance from the projected perimeter is measured in a straight line or a geodesic line. The above features may be controlled by the physician using a pop-window(s), menu option(s) and/or short-cut keys, by way of example only.

Figure 7:
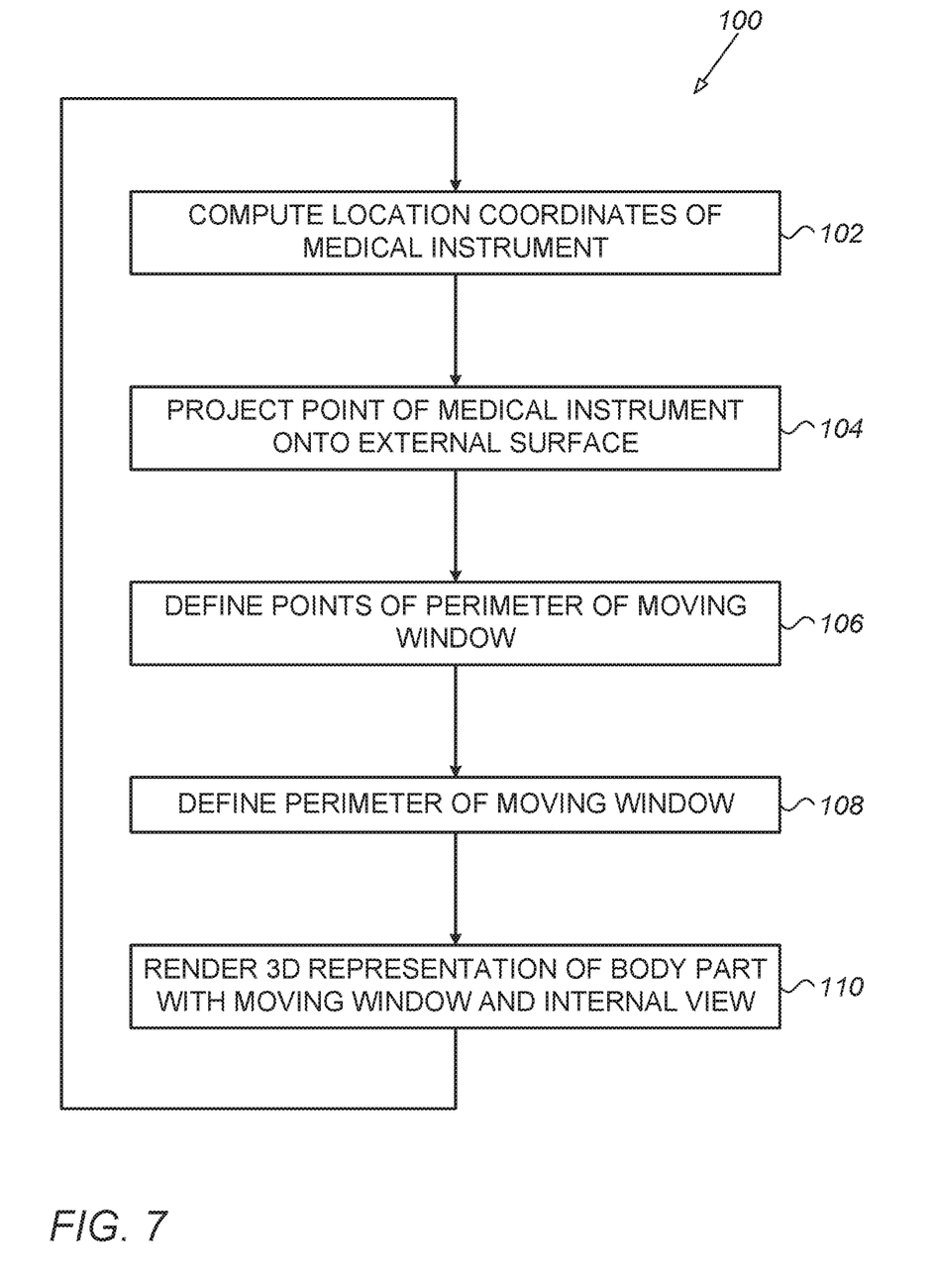
FIG. 7 is a view of a flowchart including exemplary steps in a method of operation of the apparatus of FIG. 1.

Reference is now made to FIG. 7, which is a view of a flowchart 100 including exemplary steps in a method of operation of the apparatus 12 of FIG. 1. The processing circuitry 51 is configured to compute (block 102) location coordinates of the medical instrument in the body part. The processing circuitry 51 is configured to project (block 104) a point of the medical instrument onto the external surface 74 of the 3D representation 72 of the body part. In some embodiments, the processing circuitry 51 is configured to project the point of the medical instrument onto the external surface 74 in a direction substantially perpendicular (e.g., within 5 degrees accuracy) to the external surface. In some embodiments, the processing circuitry 51 is configured to define (block 106) locations on the perimeter of the moving window 76 as terminating at the ends of respective equidistant (geodesic or straight) lines from the projected point so that the moving window 76 has a generally circular shape, which is distorted by the contours of the external surface 74 of the 3D representation 72 of the body part. The processing circuitry 51 is configured to define (block 108) the perimeter of the moving window 76 centered around the projected point.

In some embodiments, the moving window 76 may have any suitable shape (e.g., circle, ellipse, or any polygon) and any suitable size with the perimeter of the moving window 76 being centered around the projected point and/or computed to include the 3D representation 82 of the medical instrument (or a part thereof such as a distal end of the medical instrument).

The processing circuitry 51 is configured to render (block 110) the 3D representation 72 of the body part to the display 61, showing the external surface 74 with the moving window 76, which moves over the external surface 74 in the 3D representation 72 of the body part responsively to the computed location coordinates of the medical instrument so as to provide, via the window 76, the internal view 80 of the 3D representation 72 of the body part. The rendering of the 3D representation 72 may include, by way of example only, any combination of features described herein above with reference to FIGS. 3-6.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A body part visualization system, comprising:
a medical instrument configured to be inserted into a body part of a living subject; and
processing circuitry configured to:
compute location coordinates of the medical instrument in the body part; and
render to a display a first three-dimensional (3D) representation of the body part, the first 3D representation showing context of an external surface of the body part with a moving window, the moving window having a perimeter defined around a point of the medical instrument projected onto the external surface of the first 3D representation, the moving window configured to move over the external surface in the first 3D representation responsively to the computed location coordinates of the medical instrument so as to simultaneously reveal on the display, directly via the window, context of an internal view of the first 3D representation of the body part while the moving window moves over the external surface, the internal view including a second 3D image of only a distal portion the medical instrument within the body part at the computed location coordinates.

2. The body part visualization system according to claim 1, wherein the moving window includes a mesh which follows the contours of a part of the external surface replaced by the moving window.

3. The body part visualization system according to claim 2, wherein the mesh is at least partially colored to correspond to colored patches allocated to the part of the external surface.

4. The body part visualization system according to claim 1, wherein the internal view includes colored patches disposed on an internal surface of the first 3D representation.

5. The body part visualization system according to claim 1, wherein the processing circuitry is configured to project the point of the medical instrument onto the external surface in a direction substantially perpendicular to the external surface.

6. The body part visualization system according to claim 1, wherein the processing circuitry is configured to define locations on the perimeter as terminating at the ends of respective equidistant geodesic lines from the projected point.

7. The body part visualization system according to claim 1, wherein the internal view includes at least one element in addition to the second 3D representation of at least the part of the medical instrument.

8. The body part visualization system according to claim 7, wherein the body part is a chamber of a heart, the medical instrument including an ablation probe having an electrode configured to apply radio-frequency radiation to a myocardium of the chamber so as to ablate the myocardium.

9. The body part visualization system according to claim 8, wherein the at least one element includes a graphical symbol marking a location of an ablation performed by the ablation probe.

10. A body part visualization method, comprising:
computing location coordinates of a medical instrument in a body part of a living subject; and
rendering to a display a first three-dimensional (3D) representation of the body part, the first 3D representation showing context of an external surface of the body part with a moving window, the moving window having a perimeter defined around a point of the medical instrument projected onto the external surface of the first 3D representation, the moving window configured to move over the external surface in the first 3D representation responsively to the computed location coordinates of the medical instrument so as to simultaneously reveal on the display, directly via the window, context of an internal view of the first 3D representation of the body part while the moving window moves over the external surface, the internal view including a second 3D image of only a distal portion of the medical instrument within the body part at the computed location coordinates.

11. The body part visualization method according to claim 10, wherein the moving window includes a mesh which follows the contours of a part of the external surface replaced by the moving window.

12. The body part visualization method according to claim 11, wherein the mesh is at least partially colored to correspond to colored patches allocated to the part of the external surface.

13. The body part visualization method according to claim 10, wherein the internal view includes colored patches disposed on an internal surface of the first 3D representation.

14. The body part visualization method according to claim 10, wherein the projecting including projecting the point of the medical instrument onto the external surface in a direction substantially perpendicular to the external surface.

15. The body part visualization method according to claim 10, further comprising defining locations on the perimeter as terminating at the ends of respective equidistant geodesic lines from the projected point.

16. The method body part visualization according to claim 10, wherein the internal view includes at least one element in addition to the second 3D representation of at least the part of the medical instrument.

17. The body part visualization method according to claim 16, wherein the body part is a chamber of a heart, the medical instrument including an ablation probe having an electrode configured to apply radio-frequency radiation to a myocardium of the chamber so as to ablate the myocardium.

18. The body part visualization method according to claim 17, wherein the at least one element includes a graphical symbol marking a location of an ablation performed by the ablation probe.

19. A computer program product, comprising a non-transitory computer-readable medium having computer-readable program code embodied therein to be executed by one or more processors, the program code including instructions to:
compute location coordinates of a medical instrument in a body part of a living subject;
and render to a display a first three-dimensional (3D) representation of the body part, the first 3D representation showing context of an external surface of the body part with a moving window, the moving window having a perimeter defined around a point of the medical instrument projected onto the external surface of the first 3D representation, the moving window configured to move over the external surface in the first 3D representation responsively to the computed location coordinates of the medical instrument so as to simultaneously provide reveal on the display, directly via the window, context of an internal view of the first 3D representation of the body part while the moving window moves over the external surface, the internal view including a second 3D image of only a distal portion of the medical instrument within the body part at the computed location coordinates.

\* \* \* \* \*